United States Patent [19]
Luther

[11] Patent Number: 5,743,882
[45] Date of Patent: Apr. 28, 1998

[54] NEEDLE BLUNTING ASSEMBLY FOR USE WITH INTRAVASCULAR INTRODUCERS

[75] Inventor: Ronald B. Luther, Newport Beach, Calif.

[73] Assignee: Luther Medical Products, Inc., Tustin, Calif.

[21] Appl. No.: 611,323

[22] Filed: Mar. 8, 1996

[51] Int. Cl.$^6$ .................................................. A61M 5/178
[52] U.S. Cl. ........................ 604/168; 604/164; 604/165; 604/167; 604/170; 604/171; 604/192
[58] Field of Search ........................ 604/164, 165, 604/167, 168, 170, 171, 192

[56] References Cited

U.S. PATENT DOCUMENTS

| | | | |
|---|---|---|---|
| 2,623,520 | 12/1952 | Bamford, Jr. | 128/221 |
| 2,623,521 | 12/1952 | Shaw | 128/221 |
| 2,847,995 | 8/1958 | Adams | 128/214 |
| 3,344,786 | 10/1967 | Berg et al. | 128/215 |
| 3,463,152 | 8/1969 | Sorenson | 128/214.4 |
| 3,491,756 | 1/1970 | Bentov | 128/221 |
| 3,536,073 | 10/1970 | Farb | 128/214.4 |
| 3,809,081 | 5/1974 | Loveless | 128/214.4 |
| 3,923,066 | 12/1975 | Francisoud et al. | 128/348 |
| 4,233,975 | 11/1980 | Yerman | 128/218 P |
| 4,274,408 | 6/1981 | Nimrod | 128/214.4 |
| 4,417,886 | 11/1983 | Frankhouser | 604/53 |
| 4,509,945 | 4/1985 | Kramann et al. | 604/164 |
| 4,525,157 | 6/1985 | Vaillancourt | 604/52 |
| 4,529,399 | 7/1985 | Groshong et al. | 604/53 |
| 4,631,057 | 12/1986 | Mitchell | 604/198 |
| 4,652,256 | 3/1987 | Vaillancourt | 604/52 |
| 4,664,654 | 5/1987 | Strauss | 604/198 |
| 4,676,783 | 6/1987 | Jagger et al. | 604/171 |
| 4,702,738 | 10/1987 | Spencer | 604/198 |
| 4,731,068 | 3/1988 | Hesse | 604/110 |
| 4,747,831 | 5/1988 | Kulli | 604/110 |
| 4,762,516 | 8/1988 | Luther et al. | 604/164 |
| 4,772,264 | 9/1988 | Cragg | 604/168 X |
| 4,772,266 | 9/1988 | Groshong | 604/164 |
| 4,778,453 | 10/1988 | Lopez | 604/110 |
| 4,781,692 | 11/1988 | Jagger et al. | 604/164 |
| 4,826,490 | 5/1989 | Byrne et al. | 604/198 |
| 4,828,547 | 5/1989 | Sahi et al. | 604/110 |
| 4,828,549 | 5/1989 | Kvalo | 604/164 |
| 4,832,693 | 5/1989 | Gloyer | 604/110 |
| 4,832,696 | 5/1989 | Luther et al. | 604/164 |
| 4,834,718 | 5/1989 | McDonald | 604/195 |
| 4,863,431 | 9/1989 | Vaillancourt | 604/168 |
| 4,869,717 | 9/1989 | Adair | 604/51 |
| 4,944,728 | 7/1990 | Carrell et al. | 604/164 |
| 4,950,252 | 8/1990 | Luther et al. | 604/198 |
| 5,009,642 | 4/1991 | Sahi | 604/158 |
| 5,104,382 | 4/1992 | Brinkerhoff et al. | 604/165 |
| 5,221,263 | 6/1993 | Sinko et al. | 604/164 X |
| 5,312,345 | 5/1994 | Cole | 604/164 X |
| 5,380,292 | 1/1995 | Wilson | 604/164 |
| B1 4,417,886 | 1/1991 | Frankhouser | 604/53 |

*Primary Examiner*—Sam Rimell
*Assistant Examiner*—Robert V. Racunas
*Attorney, Agent, or Firm*—Stetina Bundra & Buyan

[57] ABSTRACT

A needle blunting assembly for use with intravascular introducers, needles and other cannula which are insertable into the bodies such that they become contaminated with body fluids. The blunting apparatus comprises an elongate blunting member which is disposed within the bore of the needle or other tubular cannula, and is axially moveable from a "nonblunting" position wherein the blunt distal tip of the blunting member is positioned within the bore of the needle or cannula, and a "blunting" position wherein the blunt distal tip of the blunting member protrudes out of and beyond the distal tip of the needle or cannula.

11 Claims, 3 Drawing Sheets

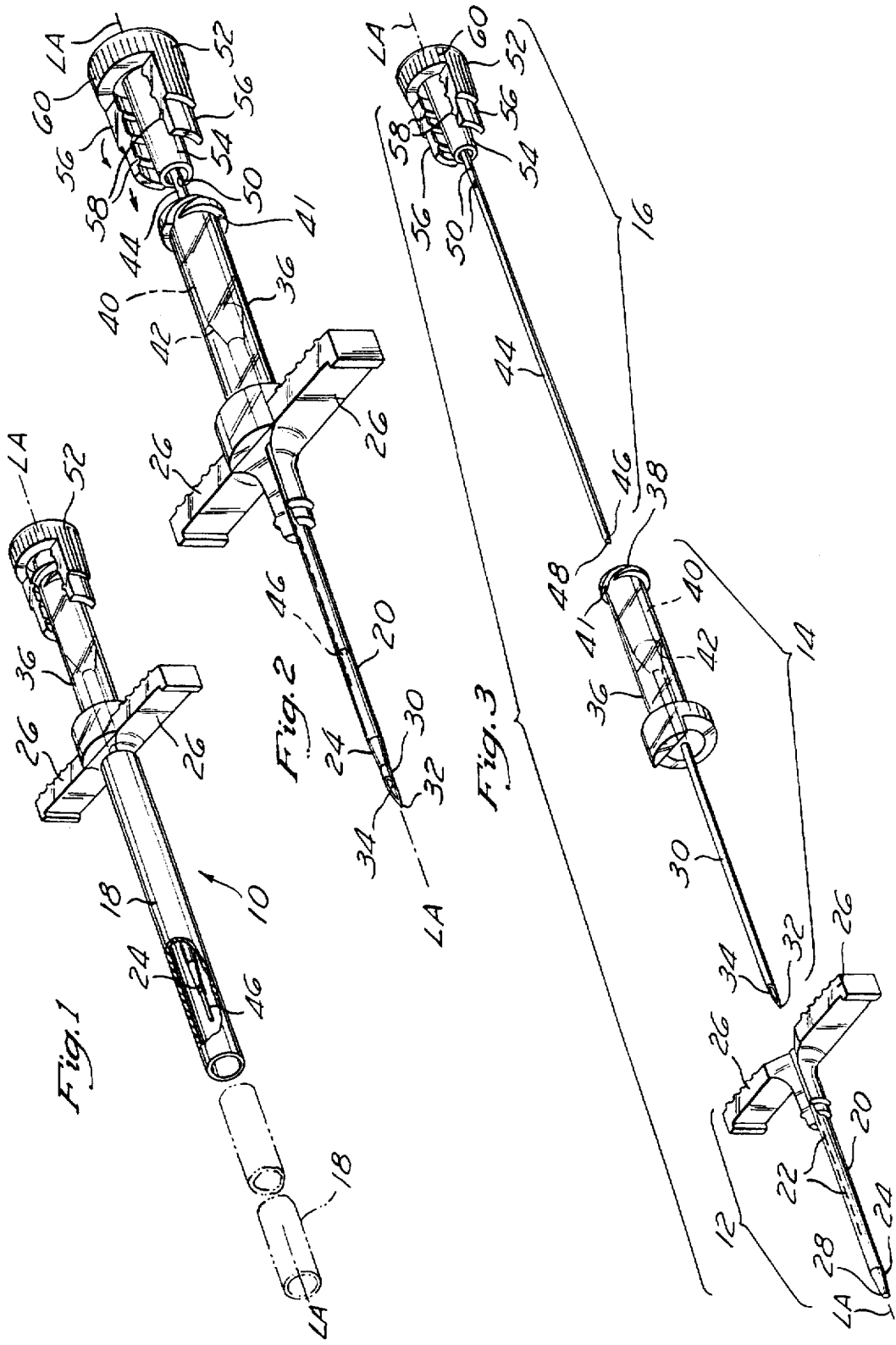

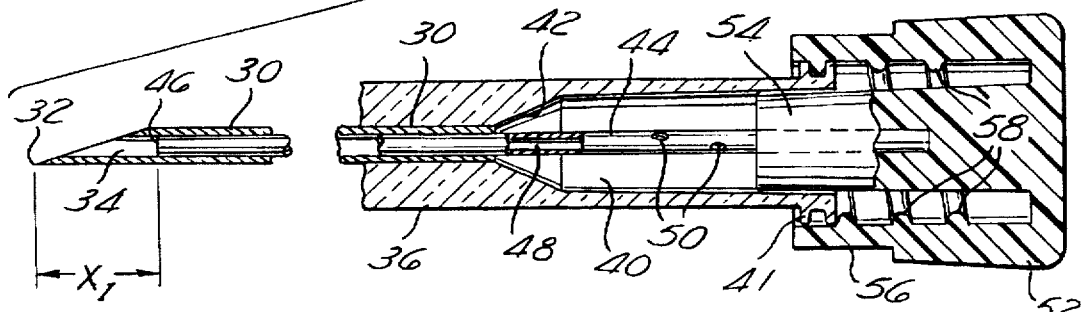
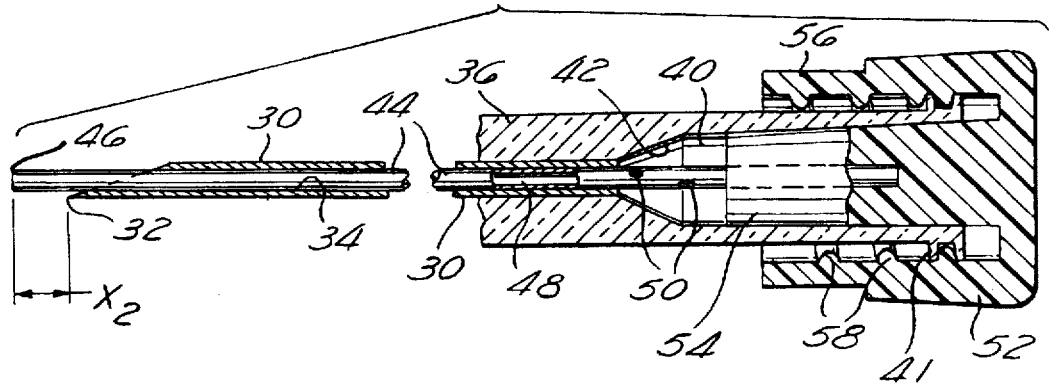
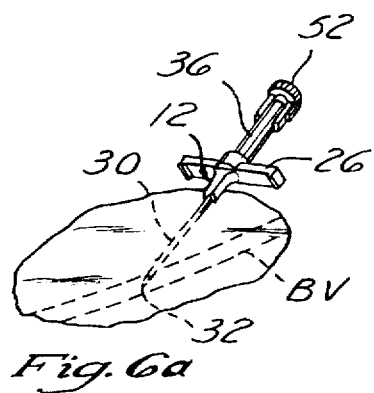
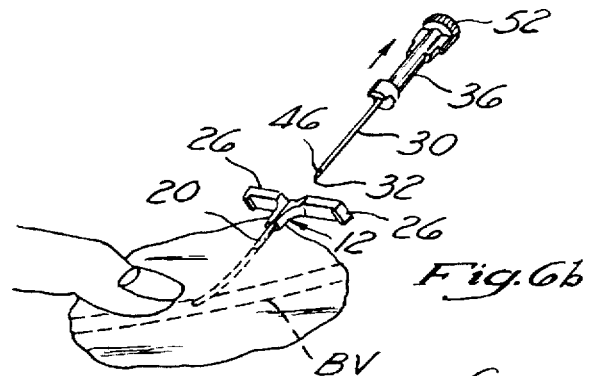
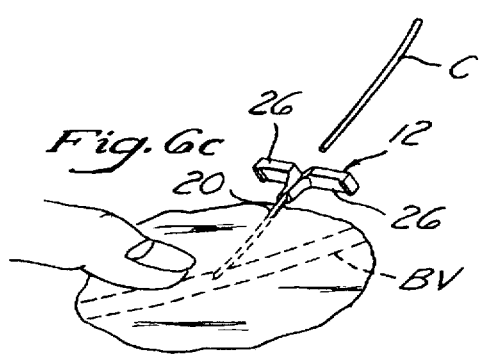
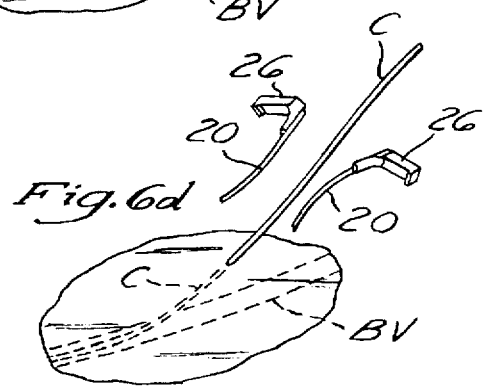

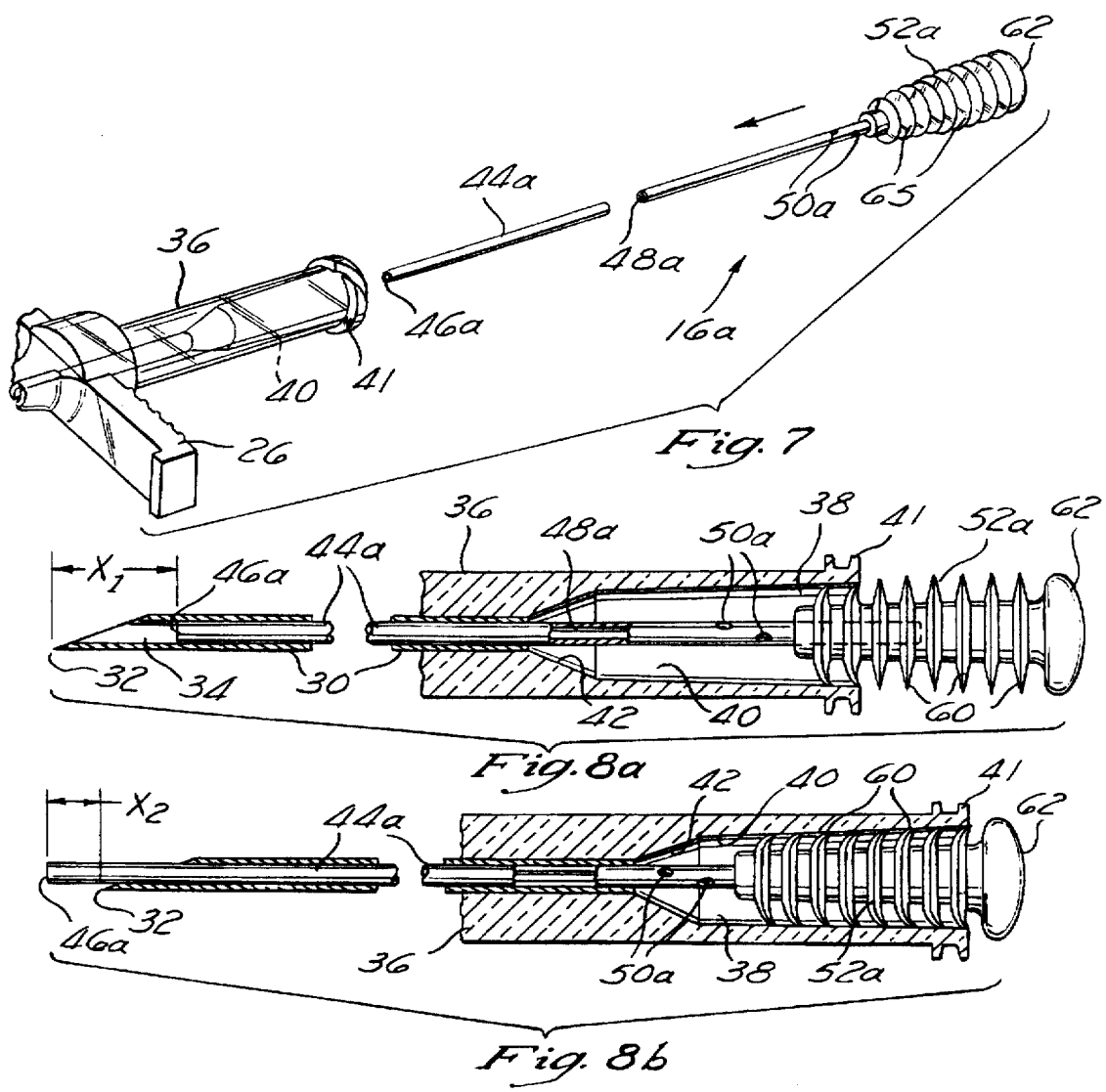

NEEDLE BLUNTING ASSEMBLY FOR USE WITH INTRAVASCULAR INTRODUCERS

FIELD OF THE INVENTION

The present invention relates generally to medical devices, and more particularly to a needle blunting apparatus which is usable to prevent inadvertent trauma to healthcare workers and other persons who handle used hypodermic needles. The present invention also relates to certain intravascular introducer sheaths, such as peel-away introducers, which incorporate needles which are equipped with the needle-blunting apparatus of the present invention.

BACKGROUND OF THE INVENTION

Healthcare workers are at risk of inadvertent needle trauma when handling used hypodermic needles, and the like. In recent years, such inadvertent needle trauma has become a cause for heightened concern in view of the increase in the incidents of serious or potentially fatal blood-borne pathogens such as human immuno-deficiency various (HIV) and hepatitis C virus.

In view of the potential for inadvertent needle trauma to cause infection of healthcare workers with blood born pathogens such as HIV and hepatitis, there exists a need to provide needle safety devices which render used hypodermic needles incapable of causing inadvertent needle trauma when handled by health care workers, trash handlers, etc.

Examples of needle safety devices which have heretofore been known for deterring or preventing inadvertent trauma by hypodermic needles (e.g., intravenous needles) include those described in U.S. Pat. Nos. 2,847,995, 3,463,152, 3,536,073, 4,631,057, 4,664,654, 4,676,783, 4,702,738, 4,747,831, 4,762,516, 4,778,453, 4,781,692, 4,826,490, 4,828,549, 4,832,696, 4,834,718, and 4,950,252.

Although many of the heretofore proposed needle safety devices and apparatus do effectively prevent or deter inadvertent needle trauma, none of these prior devices or apparatus are universally usable in connection with all types of hypodermic needles, in all applicable clinical situations. Accordingly, there remains a need for the development of additional safety devices and/or apparatus for preventing or deterring inadvertent needle sticks, especially when handling used hypodermic needles.

SUMMARY OF THE INVENTION

The present invention provides an intravascular introducer assembly which comprises the combination of a) tubular introducer sheath, b) a tubular needle having a sharpened distal tip and c) a elongate blunting member having a blunt distal tip, said elongate blunting member being disposed within the bore of said needle and axially moveable from a "non-blunting position" wherein the blunt distal tip of the blunting member is positioned within the bore of the needle, and the "blunting" position wherein the blunt distal tip of the blunting member protrudes out of and beyond the sharpened distal tip of the needle so as to deter the sharpened distal tip of the needle from causing penetration trauma.

Further in accordance with the invention, a flash chamber which is formed of at least partially of transparent material may be formed on the proximal end of the needle, and a hollow bore may extend longitudinally through at least a portion of the blunting member, in communication with at least one blood outlet opening which is formed in said blunting member and located within the flash chamber when the blunting member is in it's proximally retracted "non-blunting" position. In this embodiment, when the sharpened distal tip of the needle enters a blood vessel, blood will pass in the proximal direction through the hollow inner bore of the blunting member and will flow out of the blood outlet aperture into the flash chamber such that said blood may be visually observed by the operator as an indication that the distal tip of the needle has entered into the blood vessel.

Still further in accordance with the invention, the tubular introducer sheath may comprise any suitable type of intravascular introducer sheath, including but not necessarily limited to tearable introducer sheaths having longitudinal scores, grooves or weakened regions formed therein such that the introducer sheath may be torn into separate pieces and essentially peeled away and removed from a tubular catheter which extends through the lumen of the introducer sheath.

Still further in accordance with the invention, the needle blunting member may incorporate a positioning apparatus for alternately positioning and holding the blunting member in a) it's proximally retracted "non-blunting" position and b) it's distally advanced "blunting" position. In this regard, one embodiment of such positioning member may comprise an internally threaded proximal cap-like member formed on the proximal end of the blunting member and engageable with a thread-engaging flange formed on the proximal end of the needle member, such that partial threading of the cap-like proximal member onto the thread engagement flange will position and hold the blunting member in it's partially retracted "non-blunting" position, and subsequent further rotational advancement of the cap-like proximal member onto the thread-engaging flange will advance and hold the blunting member in it's distally advanced "blunting" position. In an alternative embodiment, the needle member may incorporate a proximal hub having an internal bore formed therein and the blunting member may incorporate a proximal positioning member having a plurality of annular engagement fins formed thereon such that only distal ones of said engagement fins may be initially advanced into the proximal bore of said needle member into frictional engagement with the wall of said proximal bore to hold the blunting member in it's proximally retracted "non-blunting" position and, thereafter, additional ones of said engagement fins may be further advanced in the distal direction into said bore so as to frictionally engage the wall of said bore, thereby causing said blunting member to move to and be held in it's distally advanced "blunting" position. Other positioning member embodiments may also be utilized as an alternative to the internally threaded proximal cap member and/or externally finned proximal engagement member described with respect to these two specific embodiments of the invention. Still further in accordance with the invention there is provided a method for positioning an over-the-needle intravascular introducer within a blood vessel, said method including the steps of a) positioning a blunting member within the bore of the introducer needle such that the blunt distal tip of the blunting member is initially disposed within the bore of the needle and b) subsequently moving the blunting member in the distal direction such that the blunt distal tip of the blunting member protrudes out of and beyond the distal tip of the needle to as to deter the distal tip of the needle from causing penetration trauma.

Further objects and advantages of the invention will become apparent to those skilled in the art upon reading and understanding of the following detailed description and the accompanying drawings.

BRIEF DESCRIPTION OF THE DRAWINGS

FIG. 1 is a perspective view of a peel-away introducer assembly incorporating a needle blunting apparatus of the present invention.

3

FIG. 2 is a perspective view of the peel-away cannula assembly of FIG. 1 following a) removal of the protective outer sheath therefrom and b) partial retraction of the needle blunting apparatus incorporated therein.

FIG. 3 is an exploded view of the peel-away cannula assembly shown in FIG. 2.

FIG. 4 is a partial longitudinal sectional view of the needle component of the peel-away cannula assembly shown in FIGS. 1-3 having the needle blunting apparatus of the present invention in it's retracted position.

FIG. 5 is a partial longitudinal sectional view of the needle component of the peel-away cannula assembly shown in FIGS. 1-3 having the needle blunting apparatus of the present invention in it's advanced "blunting" position.

FIGS. 6a, 6b, 6c and 6d are a step-wise illustration of a preferred method of using the peel-away introducer assembly shown in FIGS. 1-5.

FIG. 7 is an exploded-partial prospective view of an alternative embodiment of the needle blunting apparatus of the present invention.

FIG. 8a is a partial longitudinal sectional view showing the needle blunting apparatus of FIG. 7 in its retracted position.

FIG. 8b is a partial longitudinal sectional view showing the needle blunting apparatus of FIG. 7 in it's advanced "blunting" position.

DETAILED DESCRIPTION OF THE PREFERRED EMBODIMENTS

The following detailed description and the accompanying drawings are provided for the purpose of describing and illustrating presently preferred embodiments of the invention only, and are not intended to limit the scope of the invention in any way.

With reference to the first embodiment shown in FIGS. 1-6, there is provided a peel-away introducer assembly 10 which is usable to facilitate percutaneous insertion of intravascular cannula, tube or catheter. The assembly 10 generally comprises a peel-away introducer 12, a needle 14, a needle blunting assembly 16 and a protective outer sheath 18.

The peel-away introducer 12 comprises an elongate tubular cannula 20 having weakened areas 22 such as linear scores or perforations formed at directly opposite locations, and extending parallel to the longitudinal axis LA of the cannula 20. A hollow lumen 28 extends longitudinally through the cannula 20. A tapered distal tip 24 is formed on the distal end of the cannula 20 to facilitate insertion and advancement of the cannula through skin, connective tissue and blood vessel wall. Gripping wings 26 are formed on opposite sides of the proximal end of the cannula 20 to facilitate manipulation, use and subsequent tearing or severing of the cannula 20.

The needle component 14 of the peel-away introducer assembly 10 comprises an elongate rigid needle 30 formed of material such as stainless steel hypotubing and having a beveled or otherwise sharpened distal tip 32. A hollow bore 34 extends longitudinally through the needle 30. A transparent flash chamber housing 36 is formed on the proximal end of the elongate rigid needle 30. A hollow flash chamber bore 38 extends longitudinally through the proximal flash chamber housing 36. Such longitudinal flash chamber bore 38 has a cylindrical proximal inner wall 48 of substantially continuous diameter and a narrowed or tapered distal inner wall 42. The hollow inner bore 38 of the flash chamber

4 housing 36 is continuous with and connected to the hollow bore 34 of the needle 30.

The needle blunting apparatus 16 of the peel-away introducer assembly 10 comprises an elongate tubular blunting member 44 preferably formed of rigid material such as stainless steel hypotubing, and preferably having an outer diameter which is slightly smaller than the inner diameter of the needle bore 34. A blunt distal tip 46 is formed on the distal end of the blunting member 44 and a hollow lumen 48 extends longitudinally therethrough. Blood outlet apertures 50 are formed adjacent the proximal end of the blunting member 44 to permit blood to pass out of the hollow lumen 48 of the blunting member 44. A blunting member positioning apparatus 52 is formed on or otherwise associated with the blunting apparatus to anchor or hold the blunting member in its respective "non-blunting" and "blunting" positions. Such positioning apparatus 52 may comprise a cap like structure having a tapered cylindrical inner boss 54 located between two (2) forwardly extending outer struts 56. Each of the outer struts 56 has internal threads 58 formed thereon. A gripping surface 60 such as a series of longitudinal grooves or corrugations is preferably formed about the outer surface of the locator apparatus 52 to facilitate grasping and turning of the blunting apparatus 16 during use thereby causing the blunting member 52 to move from its proximally retracted "nonblunting" position to its distally advanced "blunting" position, as will be described more fully herebelow.

It will be appreciated from the assembly drawings of FIGS. 2 and 4 that the peel-away introducer 12, needle component 14 and blunting apparatus 16 are initially disposed in a coaxially nested arrangement as shown in FIG. 1 wherein the needle 30 extends coaxially through the lumen 28 of the cannula 20 and the blunting member 44 extends through a portion of the bore 34 of the needle 30 such that the blunt distal tip 46 of the blunting member 44 is located within the bore 34 of the needle 30 a spaced distance X, proximal to it's sharpened distal tip. Thereafter, clockwise rotation of the threads 58 about cylindrical wall 40 will cause the blunting assembly 16 to be advanced in the distal direction, while counterclockwise rotation thereof will cause the blunting assembly 16 to be retracted in the proximal direction. This accomplishes alternative positioning of the blunting apparatus 16 between its proximally retracted position (FIG. 4) and its distally extended "blunting" position (FIG. 5) with further reference to the showings of FIGS. 4 and 5, it will be appreciated that, when the blunting apparatus 16 is in its proximally retracted "non-blunting" position the blunt distal tip 36 of the tubular member 44 will reside within the lumen 34 of the elongate rigid needle 30, a spaced distance $X_1$ from the sharp distal tip 32 thereof. However, when the blunting apparatus 16 is moved to its distally advanced "blunting" position, the blunt distal tip 46 of the tubular member 44 will extend out of and beyond the sharp distal tip 32 of the elongate rigid needle 30 by a distance $X_2$. Such protrusion of the blunt distal tip 46 of the tubular member 44 beyond the sharpened distal tip 32 of the elongate rigid needle 30 effectively prevents the sharpened distal tip 32 of the elongate rigid needle causing trauma to, or puncturing, skin, or other tissue. In this regard, the blunting assembly 16, when moved to its distally advanced "blunting" position (FIG. 5) will effectively prevent inadvertent skin puncture or trauma by the sharpened distal tip 32 of the needle 14.

It will be appreciated that the proximal engagement member 52 of the blunting apparatus 16 may be formed or configured in various different ways, and in various different ways without departing from its intended functions, including the function of facilitating movement of the blunting apparatus 16 between its proximally retracted "non-blunting" position as shown in FIG. 4, and its distally extended "blunting" position as shown in FIG. 5. In this regard, one possible alternative configuration of the blunting apparatus 52 is shown in FIGS. 7–8 wherein the alternative blunting apparatus 16a comprises an elongate tubular member 44a having a blunt distal tip 46a and a hollow lumen 48a extending longitudinally therethrough. A plurality of blood outlet apertures 50a are formed adjacent the proximal end of the tubular member 44a, immediately distal to the proximal engagement member 52a. The proximal engagement member 52a of this alternative blunting apparatus 16a comprises a series of annular elastomeric engagement fins 60 which, when advanced into the inner bore 38 of the proximal flash chamber 36 of the needle 14, will engage the wall(s) of said inner bore 38 in a manner which holds the elongate tubular member 44 in a substantially fixed longitudinal position relative to the needle 14, and which deters subsequent retraction or inadvertent sliding out of the blunting apparatus 16.

The preferred operation of this alternative blunting apparatus 16a is specifically shown in FIGS. 8a and 8b. With reference to FIGS. 8a and 8b, when the alternative blunting apparatus 16a is in its proximally retracted "non-blunting" position shown in FIG. 8a, only the distal-most engagement fins 60 will be in engagement with the proximal cylindrical wall 40 of the inner bore 38 of the flash chamber 36 and the blunt distal tip 46a of the tubular member 44a will reside in the hollow lumen 34 of the rigid needle member 30 a spaced distance $X_1$ proximal to the beveled or otherwise sharpened distal tip 32 of the elongate rigid needle 30.

Thereafter, when it is desired to move the blunting apparatus 16a to its distally advanced "blunting" position shown in FIG. 8b, pressure may be applied to the rear or proximal surface 62 of the proximal engagement member 52a to force the engagement member 52a further into the hollow bore 38a of the flash chamber 360 such that the blunt distal end 46a of the elongate tubular member 44a will be advanced out of and beyond the sharp distal tip 32 of the needle 14 by a distance of $X_2$ such distal advancement of the blunting member 16a will cause the previously non-inserted elastomeric engagement fins 60 to advance into the hollow bore 38 of the flash chamber 36 such that such additional engagement fins 60 will be in abutment with, and will be proximally deflected by, the surrounding cylindrical proximal wall 40 of the hollow bore 38. In this regard, the frictional engagement and proximal deflection of the elastomeric engagement fins 60 deter the blunting apparatus 16a from being proximally retracted or inadvertently pulled out of the needle apparatus 14. Thus, once the blunting apparatus 16a has been moved to its distally advanced "blunting" position as shown in FIG. 8b, the entire needle 14 (having the blunting apparatus 16a inserted therethrough) may be extracted, removed and discarded without risk of inadvertent needle puncture or other trauma by the sharpened distal tip 32 of the needle 14.

PREFERRED MODE OF OPERATION

FIGS. 6a–6d show a preferred mode of utilizing the embodiment shown in FIGS. 1–5.

With reference to FIGS. 6a–6d the blunting apparatus 16 is initially retracted to its "non-blunting position shown in FIG. 4. The needle 14 having the introducer 12 disposed thereon is then percutaneously inserted into a blood vessel BV, as shown in FIG. 6a.

Thereafter, the blunting apparatus 16 is advanced to its distally advanced "blunting position" as shown in FIG. 5 and the needle 14 is withdrawn (FIG. 6b). Because the blunt distal tip 46 of the tubular member 40 of the blunting apparatus 16 extends by distance $X_2$ beyond the beveled or sharpened distal tip 32 of the needle 14, the needle 14 is thereby rendered incapable of puncturing or causing trauma to the user or other persons who have occasion to handle the used needle 14.

After the needle 14 and blunting apparatus 16 have been removed and discarded, a tubular catheter C is advanced through the introducer 12, as shown in FIG. 6c. Thereafter, the introducer 12 is proximally withdrawn, leaving the catheter C within the blood vessel BV. After the introducer 12 has been withdrawn such that it resides about an exteriorized portion of the catheter C, the user will grasp the opposite grasping wings 26 and will tear the introducer cannula 20 along its scores or weakened regions 22. In this regard, the introducer 12 is torn or separated in two halves, as shown in FIG. 6d. The torn or separated halves of the introducer 12 are then discarded, and the catheter C is allowed to remain indwelling within the blood vessel BV.

Those skilled in the art will recognize that the invention has been described herein with reference to certain presently preferred embodiments and methods, and no effort has been made to exhaustively describe all possible embodiments and methods by which the invention may be practiced. Indeed, various additions, deletions, modifications and alterations may be made to the above described embodiments and methods without departing from the intended spirit and scope of the invention. Accordingly, it is intended that all such additions, deletions, modifications and alterations be included within the scope of the following claims.

What is claimed is:

1. An intravascular introducer assembly, said assembly comprising:

a tubular introducer sheath having a proximal end, a distal end and a hollow lumen extending longitudinally therethrough;

a needle having a sharpened distal tip and a hollow bore extending longitudinally therethrough, said needle being initially disposed coaxially within the lumen of said introducer sheath such that the sharpened distal tip of the needle protrudes out of and beyond the distal end of said introducer sheath;

an elongate blunting member having a hollow lumen extending longitudinally therethrough, a closed proximal end, and a blunt distal tip, said elongate blunting member being disposed coaxially within the bore of said needle;

said blunting member being axially moveable from a non-blunting position wherein the blunt distal tip of said blunting member is positioned within the bore of said needle a spaced distance proximal to the sharpened distal tip of said needle, to a distally advanced blunting position wherein the blunt distal tip of said blunting member protrudes out of and beyond the sharpened distal tip of said needle to deter the sharpened distal tip of said needle from causing penetration trauma.

2. The assembly of claim 1 wherein said needle further comprises:

an at least partially transparent flash chamber formed on the proximal end of said needle; and, wherein said blunting apparatus further comprises:

a blood inlet opening formed in the distal tip of said blunting member;

at least one blood outlet opening formed in said blunting member at a location which is within said transparent flash chamber when said blunting apparatus is in it's proximally retracted non-blunting position; and, a lumen which extends longitudinally through said blunting member from said blood inlet aperture to said at least one blood outlet aperture;

said assembly being thereby operative such that when the distal end of said needle enters a blood vessel, blood from the lumen of the blood vessel will enter the bore of said needle through said blood inlet aperture, and said blood will then flow out of said at least one blood outlet aperture and into said flash chamber such that the presence of blood within the flash chamber is visible through at least a transparent portion of the flash chamber.

3. The assembly of claim 1 further comprising:

a blunting member positioning apparatus associated with said blunting member to alternately hold said blunting member in either it's a) proximally retracted non-blunting position or b) it's distally advanced blunting position.

4. The assembly of claim 3 wherein said blunting member positioning apparatus comprises:

- a cap-like member formed on the proximal end of said blunting member and having an internal threaded surface formed thereon, the internally threaded surface of said cap-like member being threadably engageable with the proximal end of said needle such that:
  i) when the internally threaded surface of said cap-like member is rotatably advanced onto said needle to a first position, said blunting member will be thereby held in it's proximally retracted non-blunting position; and,
  ii) when the internally threaded surface of said cap-like member is further rotatably advanced to a second position, said blunting member will be thereby advanced to and held in its distally advanced blunting position.

5. The assembly of claim 3 wherein a proximal hub having a hollow inner bore is formed on the proximal end of said needle, and wherein said blunting member locator apparatus comprises:

a series of pliable annular engagement fins formed about said blunting member adjacent the proximal end thereof, said annular fins being advanceable into the hollow bore of the proximal hub of said needle such that said engagement fins will frictionally engage said hub of said needle to hold said blunting member in a substantially fixed longitudinal position relative to said needle;

said pliable annular engagement fins being further formed on said blunting apparatus such that;
  i) distally located ones of said engagement fins may be advanced into the hollow bore of said needle hub to a first position wherein said distally located one of said engagement fins will frictionally engage the hub of said needle such that said blunting member will be thereby positioned and held in it's proximally retracted non-blunting position; and, thereafter,
  ii) additional ones of said engagement fins may be advanced into the hollow bore of said needle hub to a second position, wherein said additional ones of said engagement fins will frictionally engage the hub of said needle such that said blunting member will thereby be advanced to and held in it's distally advanced blunting position.

6. The assembly of claim 1 wherein said introducer sheath further comprises:

at least two generally linear weakened areas extending longitudinally along opposite sides of said sheath, said weakened areas being more readily tearable than the remainder of said sheath, to facilitate longitudinal tearing of said sheath into at least two separate portions.

7. The assembly of claim 6 wherein said at least two generally linear weakened areas comprise grooves.

8. The assembly of claim 6 wherein said at least two generally linear weakened areas comprise perforations.

9. The assembly of claim 6 wherein said at least two generally linear weakened areas comprise scores.

10. The assembly of claim 2 wherein a thread-engaging flange is formed on said flash chamber, and wherein a blunting member positioning apparatus having an internally threaded surface is formed on the proximal end of said blunting member, the internally threaded surface of said blunting member positioning apparatus being threadably engageable with the thread-engaging flange formed on said flash chamber such that:
  i) when the internally threaded surface of said blunting member positioning apparatus is rotatably advanced onto said needle to a first position, said blunting member will be thereby held in it's proximally retracted non-blunting position; and,
  ii) when the internally threaded surface of said cap-like member is further rotatably advanced to a second position, said blunting member will be thereby advanced to and held in its distally advanced blunting position.

11. The assembly of claim 2 wherein a hollow receiving bore having an inner bore surface extends longitudinally into the proximal end of said flash chamber, and wherein a blunting member position apparatus is formed on the proximal end of said blunting member, a series of pliable annular engagement fins being formed about said blunting member positioning apparatus, said annular engagement fins being advancable into said hollow receiving bore formed in said flash chamber such that;
  i) only distally located ones of said engagement fins may be initially advanced into the receiving bore formed in said flash chamber such that the distally located ones of said engagement fins which are then located within said hollow bore surface thereof, thereby holding said blunting apparatus in its proximally retracted non-blunting position; and, thereafter,
  ii) additional ones of said engagement fins may be advanced into the hollow bore formed in said flash chamber such that said additional ones of said engagement fins will then engage the inner bore surface thereof, thereby holding said blunting member in its distally advanced blunting position.

* * * * *